(12) United States Patent
Fackler et al.

(10) Patent No.: US 12,241,105 B2
(45) Date of Patent: *Mar. 4, 2025

(54) RECOMBINANT MICROORGANISMS AND USES THEREFOR

(71) Applicant: LanzaTech, Inc., Skokie, IL (US)

(72) Inventors: Nicholas Alexander Fackler, Chicago, IL (US); Sean Dennis Simpson, Evanston, IL (US); Michael Koepke, Chicago, IL (US); Stephanie Rhianon Jones, Evanston, IL (US)

(73) Assignee: LanzaTech, Inc., Skokie, IL (US)

( * ) Notice: Subject to any disclaimer, the term of this patent is extended or adjusted under 35 U.S.C. 154(b) by 1 day.

This patent is subject to a terminal disclaimer.

(21) Appl. No.: 17/813,240

(22) Filed: Jul. 18, 2022

(65) Prior Publication Data

US 2023/0129301 A1    Apr. 27, 2023

Related U.S. Application Data

(60) Provisional application No. 63/223,952, filed on Jul. 20, 2021.

(51) Int. Cl.
| | | |
|---|---|---|
| *C12P 19/34* | (2006.01) | |
| *C12N 1/20* | (2006.01) | |
| *C12N 1/32* | (2006.01) | |
| *C12P 7/04* | (2006.01) | |
| *G16B 5/10* | (2019.01) | |
| *G16B 20/50* | (2019.01) | |

(52) U.S. Cl.
CPC .......... *C12P 19/34* (2013.01); *C12N 1/20* (2013.01); *C12N 1/32* (2013.01); *C12P 7/04* (2013.01); *G16B 5/10* (2019.02); *G16B 20/50* (2019.02)

(58) Field of Classification Search
CPC .. C12P 19/34; C12P 7/04; C12P 5/007; C12P 5/026; C12P 7/26; C12P 7/30; C12P 7/40; C12P 7/42; C12P 7/44; C12P 7/50; C12P 7/52; C12P 7/16; C12P 7/18; C12P 21/02; C12N 1/20; C12N 1/32; C12N 9/0006; C12N 9/0008; C12N 9/0014; C12N 9/1029; C12N 9/1217; C12N 9/88; C12N 15/74

See application file for complete search history.

(56) References Cited

U.S. PATENT DOCUMENTS

| | | |
|---|---|---|
| 5,593,886 A | 1/1997 | Gaddy |
| 6,368,819 B1 | 4/2002 | Gaddy et al. |
| 7,704,723 B2 | 4/2010 | Huhnke |
| 7,972,824 B2 | 7/2011 | Simpson |
| 8,222,013 B2 | 7/2012 | Simpson |
| 8,293,509 B2 | 10/2012 | Simpson |
| 8,658,408 B2 | 2/2014 | Simpson |
| 8,900,836 B2 | 12/2014 | Simpson |
| 9,068,202 B2 | 6/2015 | Tran |
| 9,284,564 B2 | 3/2016 | Mueller |
| 9,347,076 B2 | 5/2016 | Liew |
| 9,359,611 B2 | 6/2016 | Koepke |
| 9,410,130 B2 | 8/2016 | Koepke |
| 9,738,875 B2 | 8/2017 | Koepke |
| 9,890,384 B2 | 2/2018 | Mueller |
| 9,994,878 B2 | 6/2018 | Koepke |
| 10,174,303 B2 | 1/2019 | Behrendorff |
| 10,494,600 B2 | 12/2019 | Heijstra |
| 10,590,406 B2 | 3/2020 | Koepke |
| 10,913,958 B2 | 2/2021 | Koepke |
| 2008/0107601 A1 | 5/2008 | Lauwereys et al. |
| 2012/0045807 A1 | 2/2012 | Simpson |
| 2013/0157322 A1 | 6/2013 | Simpson |
| 2016/0244785 A1 | 8/2016 | Koepke |
| 2019/0185888 A1 | 6/2019 | Koepke |
| 2021/0292732 A1 | 9/2021 | Liew |
| 2023/0050887 A1* | 2/2023 | Fackler ............... C12N 15/117 |

FOREIGN PATENT DOCUMENTS

| | | |
|---|---|---|
| KR | 20120112254 A | 10/2012 |
| WO | 2021072399 A1 | 4/2021 |

OTHER PUBLICATIONS

Wellner et al. (Rapid generation of potent antibodies by autonomous hypermutation in yeast. Nature Chemical Biology (Epub Jul. 1, 2021), 17: 1057-1064) (Year: 2021).*

Whisstock et al. Quaterly Reviews of Biophysics, 2003, "Prediction of protein function from protein sequence and structure", 36(3): 307-340. (Year: 2003).*

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*

Kisselev L., Polypeptide release factors in prokaryotes and eukaryotes: same function, different structure. Structure, 2002, vol. 10: 8-9. (Year: 2002).*

Shin, Y. O., "Microorganisms for the production of monoclonal antibodies and antibody fragments", ReSEAT Program, High-tech information analysis, 2014, pp. 1-5. (with English translation—total 12 pages).

Spadiut et al., "Microbials for the production of monoclonal antibodies and antibody fragments", Trends in Biotechnology, 2014, vol. 32, No. 1, pp. 54-60.

(Continued)

*Primary Examiner* — Iqbal H Chowdhury

(57) ABSTRACT

The disclosure provides genetically engineered C1-fixing microorganisms capable of producing nanobodies. Additionally, the disclosure provides engineered microorganisms comprising one or more disrupted genes to strategically divert carbon flux away from nonessential or undesirable products towards products and/or co-products of interest. The disclosure enables co-production of useful chemicals from gaseous substrates.

8 Claims, 2 Drawing Sheets

Specification includes a Sequence Listing.

(56) References Cited

OTHER PUBLICATIONS

International Search Report and Written Opinion issued in corresponding International Application No. PCT/US2022/073855 dated Nov. 11, 2022, 10 pages.
International Search Report and Written Opinion issued in corresponding International Application No. PCT/US2022/073858 dated Nov. 11, 2022, 11 pages.
Lee, Y. J. et al, "Challenges to production of antibodies in bacteria and yeast", Journal of Bioscience and Bioengineering, 2015, vol. 120, No. 5, pp. 483-490.
Abrini, Arch Microbiol, 161: 345-351, 1994.
Cardoso et al. "Cameo: A Python Library for Computer Aided Metabolic Engineering and Optimization of Cell Factories," ACS Synth. Biol. 2018, 7, 1163-1166. DOI: 10.1021/acssynbio.7b00423.
Drake, Acetogenic Prokaryotes, In: The Prokaryotes, 3rd edition, p. 354, New York, NY, 2006.
Ebrahim., COBRApy: COnstraints-Based Reconstruction and Analysis for Python, BMC Syst Biol, 7: 74, 2013.
Harmsen and Haard (2007) Appl. Microbiol. Biotechnol. 77 (1): 13-22.
Heap, J Microbiol Methods 78: 79-85, 2009.
Jensen, Optlang: An Algebraic Modeling Language for Mathematical Optimization, The Journal of Open Source Software, 2, doi:10.21105/joss.00139, 2017.
Karim et al. Synthetic Biology 2020; 5(1): ysaa019.
Köpke, Curr Opin Biotechnol, 22: 320-325, 2011.
Liu et al. "Predicting proteome allocation, overflow metabolism, and metal requirements in a model acetogen" PLoS PLOS Computational Biology 15(3): e1006848. pp. 1-16, Mar. 7, 2019 https://doi.org/10.1371/journal.pcbi.1006848.
Maia, Proceedings of the Genetic and Evolutionary Computation Conference Companion on—GECCO '17, New York, New York, ACM Press, 1661-1668, 2017.
Marcellin, Green Chem, 18: 3020-3028, 2016.
OBrien et al. "Using Genome-scale Models to Predict Biological Capabilities" Cell, vol. 161, Issue 5, pp. 971-987, May 21, 2015. https://doi.org/10.1016/j.cell.2015.05.019.
Perez, Biotechnol Bioeng, 110:1066-1077, 2012.
Ragsdale, Biochim Biophys Acta, 1784: 1873-1898, 2008.
Ruano-Gallego et al., "Screening and purification of nanobodies from *E. coli* culture supernatants using the hemolysin secretion system," Microb Cell Fact (2019) 18:47, pp. 1-13. https://doi.org/10.1186/s12934-019-1094-0.
Schmidt, Protein Expr Purif 92: 54-61, 2013.
Sonnenschein et al., "Biosustain/Cameo: 0.11.0," Zenodo, Jul. 28, 2017, 5 pages. doi:10.5281/zenodo.835730.
Tanner, Int J System Bacteriol, 43: 232-236, 1993.
Thiele, Nature Protocols, 5: 93-121, 2010.
Tirado-Acevedo, Production of bioethanol from synthesis gas using Clostridium ljungdahlii, PhD thesis, North Carolina State University, 2010.

* cited by examiner

RECOMBINANT MICROORGANISMS AND USES THEREFOR

CROSS REFERENCE TO RELATED APPLICATIONS

This application claims the benefit of U.S. Provisional Patent Application No. 63/223,952, filed Jul. 20, 2021, the entirety of which is incorporated herein by reference.

REFERENCE TO A SEQUENCE LISTING

The application contains a Sequence Listing which has been submitted electronically in ST.26 Sequence listing XML format and is hereby incorporated by reference in its entirety. Said ST.26 Sequence listing XML, created on Jul. 15, 2022, is named LT212US1-Sequences.xml and is 7,028 bytes in size.

FIELD

This application relates to genetically engineered microorganisms and use of those microorganisms for the fermentative production of products and optionally co-products from substrates comprising carbon dioxide ($CO_2$), carbon monoxide (CO), and/or hydrogen ($H_2$).

BACKGROUND

It has long been recognized that catalytic processes, such as the Fischer-Tropsch process, may be used to convert gases containing carbon dioxide ($CO_2$), carbon monoxide (CO), and/or hydrogen ($H_2$), such as industrial waste gas or syngas, into a variety of fuels and chemicals. Recently, however, gas fermentation has emerged as an alternative platform for the biological fixation of such gases. In particular, C1-fixing microorganisms have been demonstrated to convert gases containing $CO_2$, CO, and/or $H_2$ into products such as ethanol and 2,3-butanediol. Efficient production of such products may be limited, however, by slow microbial growth, limited gas uptake, sensitivity to toxins, or diversion of carbon substrates into undesired byproducts. Accordingly, there remains a need for genetically engineered microorganisms having improved characteristics.

SUMMARY

One embodiment is directed to a genetically engineered C1-fixing microorganism capable of co-producing at least one target product and a nanobody comprising an exogenous nucleic acid encoding a nanobody gene, wherein the genetically engineered C1-fixing microorganism has improved carbon flux through acetoacetyl-CoA compared to a parental microorganism.

The microorganism of one embodiment, wherein the at least one target product is selected from the group 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, chorismate-derived products, 3-hydroxybutyrate, 1,3-butanediol, 2-hydroxyisobutyrate or 2-hydroxyisobutyric acid, isobutylene, adipic acid, ketoadipic acid, 1,3-hexanediol, 3-methyl-2-butanol, 2-buten-1-ol, isovalerate, isoamyl alcohol, or monoethylene glycol.

The microorganism of one embodiment, wherein the nanobody targets a viral antigen.

The microorganism of one embodiment, wherein the viral antigen is a betacoronavirus antigen.

The microorganism of one embodiment, wherein the betacoronavirus antigen is a SARS-COV-2 antigen.

The microorganism of one embodiment, wherein the nanobody is contained in the microorganism.

The microorganism of one embodiment, further comprising a disruptive mutation in one or more genes.

The microorganism of one embodiment, wherein the parental microorganism is selected from the group consisting of *Acetobacterium woodii*, *Alkalibaculum bacchii*, *Blautia producta*, *Butyribacterium methylotrophicum*, *Clostridium aceticum*, *Clostridium autoethanogenum*, *Clostridium carboxidivorans*, *Clostridium coskatii*, *Clostridium drakei*, *Clostridium formicoaceticum*, *Clostridium ljungdahlii*, *Clostridium magnum*, *Clostridium ragsdalei*, *Clostridium scatologenes*, *Eubacterium limosum*, *Moorella thermautotrophica*, *Moorella thermoacetica*, *Oxobacter pfennigii*, *Sporomusa ovata*, *Sporomusa silvacetica*, *Sporomusa sphaeroides*, *Cupriavidus necator* and *Thermoanaerobacter kivui*.

The microorganism of one embodiment, wherein the parental microorganism is selected from the group consisting of *Clostridium autoethanogenum*, *Clostridium ljungdahlii*, and *Clostridium ragsdalei*.

One embodiment is directed to a method of co-producing at least one target product and a nanobody by culturing the genetically engineered C1-fixing microorganism of claim 1 in the presence of a gaseous substrate comprising one or more of CO, $CO_2$, and $H_2$.

The method of one embodiment, wherein the at least one target product is selected from the group 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, chorismate-derived products, 3-hydroxybutyrate, 1,3-butanediol, 2-hydroxyisobutyrate or 2-hydroxyisobutyric acid, isobutylene, adipic acid, ketoadipic acid, 1,3-hexanediol, 3-methyl-2-butanol, 2-buten-1-ol, isovalerate, isoamyl alcohol, or monoethylene glycol.

One embodiment is directed to a genetically engineered C1-fixing microorganism capable of producing a nanobody comprising an exogenous nucleic acid encoding a nanobody gene.

The microorganism of an embodiment, wherein the nanobody targets a viral antigen.

The microorganism of an embodiment, wherein the viral antigen is a betacoronavirus antigen.

The microorganism of an embodiment, wherein the viral antigen is a SARS-COV-2 antigen.

The microorganism of an embodiment, further comprising a disruptive mutation in one or more genes.

The microorganism of an embodiment, wherein the genetically engineered C1-fixing microorganism is selected from the group consisting of *Acetobacterium woodii*, *Alkalibaculum bacchii*, *Blautia producta*, *Butyribacterium methylotrophicum*, *Clostridium aceticum*, *Clostridium autoethanogenum*, *Clostridium carboxidivorans*, *Clostridium coskatii*, *Clostridium drakei*, *Clostridium formicoaceticum*, *Clostridium ljungdahlii*, *Clostridium magnum*, *Clostridium ragsdalei*, *Clostridium scatologenes*, *Eubacterium limosum*, *Moorella thermautotrophica*, *Moorella thermoacetica*, *Oxobacter pfennigii*, *Sporomusa ovata*, *Sporomusa silvacetica*, *Sporomusa sphaeroides*, *Cupriavidus necator*, and *Thermoanaerobacter kivui*.

The microorganism of an embodiment, wherein the genetically engineered C1-fixing microorganism is selected from the group consisting of *Clostridium autoethanogenum*, *Clostridium ljungdahlii*, and *Clostridium ragsdalei*.

One embodiment is directed to a method of producing a nanobody by culturing the genetically engineered C1-fixing microorganism in the presence of a gaseous substrate comprising one or more of CO, $CO_2$, and $H_2$.

The method of an embodiment, further comprising employing the nanobody in a diagnostic or therapeutic application.

One embodiment is a method of producing a nanobody and a co-product comprising:
a) identifying at least one nanobody within a known variant library;
b) engineering a C1-fixing microorganism capable of co-producing the nanobody and the at least one co-product, wherein the microorganism comprises an exogenous nucleic acid encoding a nanobody gene; and
c) culturing the C1-fixing microorganism in the presence of a gaseous substrate comprising one or more of CO, $CO_2$, and $H_2$ to produce the nanobody and the co-product.

DETAILED DESCRIPTION

Figure 1:
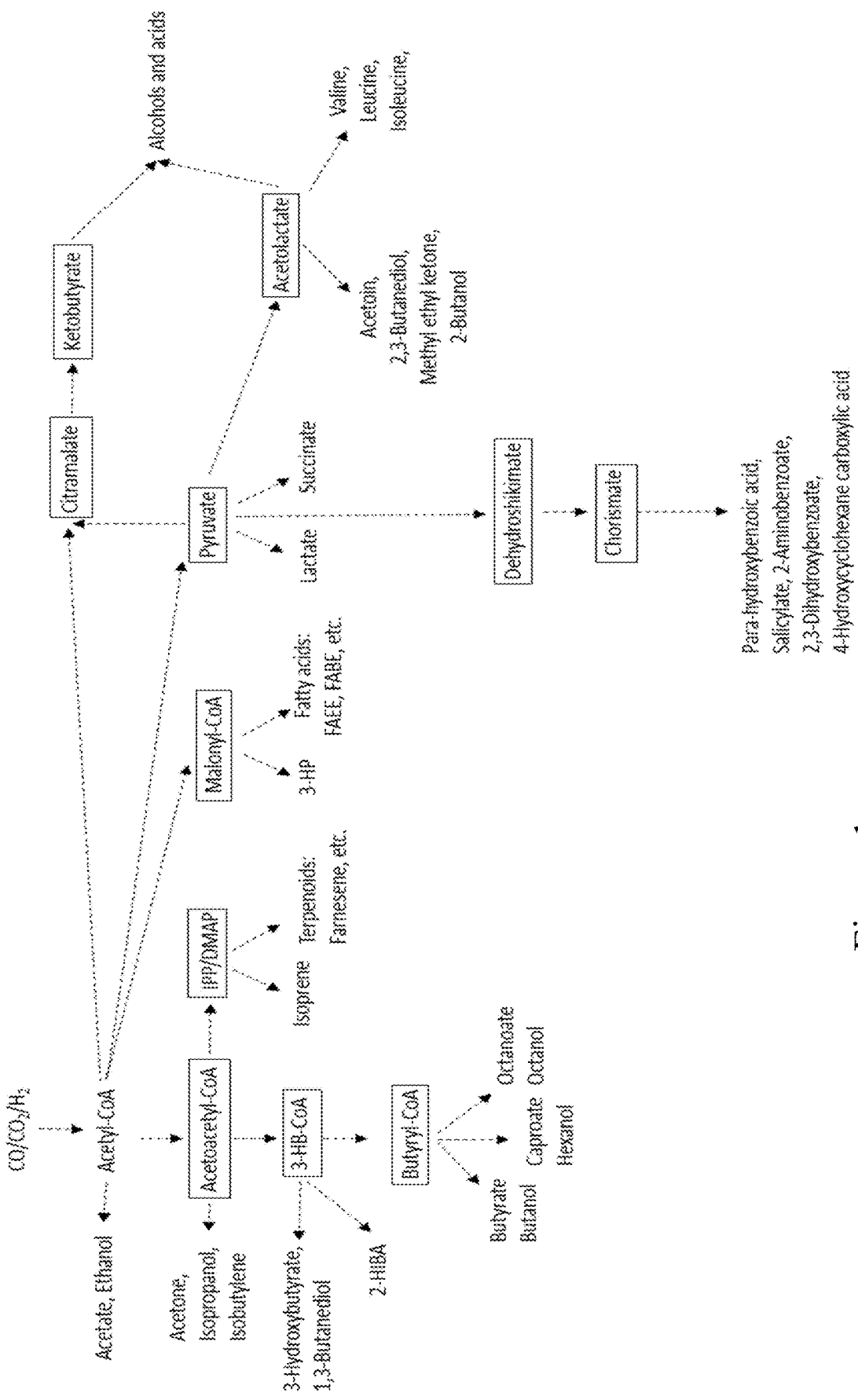
FIG. 1 is a diagram showing key production pathways and key metabolic nodes (indicated with boxes) in Wood-Ljungdahl microorganisms. Improving carbon flux through these nodes, e.g. by disrupting expression of certain genes, improves production of downstream products and optionally co-products.

The disclosure provides a genetically engineered C1-fixing microorganism capable of co-producing at least one target product and a nanobody comprising an exogenous nucleic acid encoding a nanobody gene, wherein the genetically engineered C1-fixing microorganism has improved carbon flux through acetoacetyl-CoA compared to a parental microorganism.

The disclosure provides genetically engineered microorganisms comprising at least one disrupted gene. In the microorganisms of the disclosure, carbon flux is strategically diverted away from nonessential or undesirable products and towards products and optionally co-products of interest. In certain embodiments, these disrupted genes divert carbon flux away from nonessential or undesirable metabolic nodes and through target metabolic nodes to improve production of products and optionally co-products downstream of those target metabolic nodes.

The microorganisms of the disclosure are derived from parental bacteria such as *Acetobacterium woodii*, *Alkalibaculum bacchii*, *Blautia producta*, *Butyribacterium methylotrophicum*, *Clostridium aceticum*, *Clostridium autoethanogenum*, *Clostridium carboxidivorans*, *Clostridium coskatii*, *Clostridium drakei*, *Clostridium formicoaceticum*, *Clostridium ljungdahlii*, *Clostridium magnum*, *Clostridium ragsdalei*, *Clostridium scatologenes*, *Eubacterium limosum*, *Moorella thermautotrophica*, *Moorella thermoacetica*, *Oxobacter pfennigii*, *Sporomusa ovata*, *Sporomusa silvacetica*, *Sporomusa sphaeroides*, *Cupriavidus necator*, or *Thermoanaerobacter kivui*. In one embodiment, the parental bacterium is *Clostridium autoethanogenum*, *Clostridium ljung-* *dahlii*, or *Clostridium ragsdalei*. In another embodiment, the parental bacterium is *Clostridium ljungdahlii*.

In one embodiment, the disclosure provides a genetically engineered Wood-Ljungdahl bacterium comprising a heterologous thiolase and a disruptive mutation in one or more genes encoding, for example, one or more of NAD-dependent electron-bifurcating [FeFe]-hydrogenase, glutamate synthase, citramalate synthase, acetolactate decarboxylase, lactate dehydrogenase, acetate kinase, phosphate transacetylase, and aldehyde dehydrogenase, wherein the genetically engineered bacterium has improved carbon flux through acetoacetyl-CoA compared to a parental bacterium. In one embodiment, the expression of the one or more genes is decreased or eliminated compared to the parental bacterium.

In such an embodiment, the genetically engineered bacterium may produce a product and optionally a co-product such as acetone, isopropanol, ethanol, 3-hydroxyisovaleryl-CoA, 3-hydroxyisovalerate, isobutylene, isopentenyl pyrophosphate, dimethylallyl pyrophosphate, isoprene, farnesene, 3-hydroxybutyryl-CoA, crotonyl-CoA, 3-hydroxybutyrate, 3-hydroxybutyrylaldehyde, 1,3-butanediol, 2-hydroxyisobutyryl-CoA, 2-hydroxyisobutyrate, butyryl-CoA, butyrate, butanol, caproate, hexanol, octanoate, octanol, 1,3-hexanediol, 2-buten-1-ol, isovaleryl-CoA, isovalerate, ethanol, or isoamyl alcohol. In another embodiment, the genetically engineered bacterium may produce a product and optionally a co-product, such as a nanobody. In one embodiment, the microorganism only produces a nanobody.

In one embodiment, the genetically engineered microorganism produces an immunological bioactive agent. In another embodiment, the genetically engineered microorganism produces an immunological bioactive protein. In one embodiment, the genetically engineered microorganism produces a nanobody.

In one embodiment, the nanobodies obtained from the genetically engineered microorganism have therapeutic effects and are useful for the treatment or prevention of disease or health disorders, and are useful for diagnostic testing. In one embodiment, the nanobody production platform has potential applications in generation of nanobody-based diagnostics and drug development.

Nanobodies are single domain antibodies (sdAb) typically consisting of a single monomeric variable antibody domain. Like whole antibodies (intact immunoglobulins) nanobodies are able to bind selectively to a specific antigen. With a molecular weight typically ranging from about 12 kDa to about 15 kDa, the single-domain nanobodies are much smaller than intact immunoglobulins which are typically composed of two heavy protein chains and two light chains. Nanobodies are also typically smaller than Fab fragments (about 50 kDa, one light chain and half a heavy chain) and single-chain variable fragments (about 25 kDa, two variable domains, one from a light and one from a heavy chain).

Methods of producing nanobodies are described, inter alia, by Harmsen and Haard (2007) Appl. Microbiol. Biotechnol. 77 (1): 13-22). As well, they are easily isolated using the same phage panning procedure used for traditional antibodies, allowing them to be cultured in vitro in large concentrations. The smaller size and single domain make these antibodies easier to transform into bacterial cells for bulk production, making them particularly useful for research purposes. Typically the single-domain antibody is a peptide chain about 110 amino acids long, comprising one variable domain (VH) of a heavy-chain antibody, or of a common IgG. These peptides have similar affinity to antigens as whole antibodies, but are more heat-resistant and stable towards detergents and high concentrations of urea.

The comparatively low molecular mass of nanobodies often leads to better permeability in tissues, and to a short plasma half-life since they are eliminated renally. Unlike whole antibodies, they do not show complement system triggered cytotoxicity because they lack an Fc region. However, in certain embodiments, it is contemplated that an immunoglobulin Fc region (or variant Fc region) can be fused to the nanobody to provide additional functionality.

In one embodiment, the disclosure provides a nanobody comprising a variable domain of an antibody, wherein the nanobody is contained within a genetically engineered bacteria strain. In some embodiments the variable domain is a heavy chain variable domain. In some embodiments, the antibody is a mammalian antibody. In some embodiments, the mammalian antibody is a camelid antibody. In some embodiments, the antibody is a fish antibody. In some embodiments, the nanobody comprises an affinity tag. In some embodiments, the affinity tag binds to an immobile substrate. In some embodiments, the immobile substrate is a cellulose substrate.

In another embodiment, the nanobody is conjugated to a drug. In one embodiment, the nanobody comprises an affinity tag. In an embodiment, the affinity tag binds to an immobile substrate. In one embodiment, the immobile substrate is a cellulose substrate. In one embodiment, the nanobody is conjugated to a label. In one embodiment, the nanobody binds to a target antigen. In another embodiment, the target antigen is a small molecule. In one embodiment, the nanobody is adapted to bind and purify other small molecules.

In one embodiment, the disclosure provides a method of producing the nanobody as described herein, comprising the steps of a) expressing the vector as described herein in a bacteria strain; and b) harvesting the nanobody from the bacteria strain or a cell culture supernatant of the bacteria strain. In some embodiments, the nanobody described herein comprises an affinity tag. In some embodiments, the method further comprises isolating the nanobody on an immobile substrate by binding of the affinity tag to the immobile substrate. In some embodiments, the immobile substrate is a cellulose substrate. In some embodiments, the bacteria strain secretes the nanobody.

One embodiment is a method of detecting the presence of a target antigen in a sample comprising incubating the nanobody as described herein with the sample, wherein the nanobody comprises a detectable label. In some embodiments, the target antigen is a small molecule. In some embodiments, the target antigen is a viral antigen. In some embodiments, the viral antigen is a betacoronavirus antigen. In another embodiment, the viral antigen is a SARS-COV-2 antigen. In some embodiments, the SARS-COV-2 antigen is a spike glycoprotein. In some embodiments, the viral antigen is a hepatitis B antigen.

In one embodiment, the disclosure provides a kit for detecting a target antigen in a sample, comprising a device for collecting the sample and reagents for detecting the target antigen, wherein the reagents comprise the nanobody as described herein and wherein the nanobody comprises a detectable label. In some embodiments, the target antigen is a small molecule.

In one embodiment, the genetically engineered microorganism can be used as a source of nanobodies described herein. In another embodiment, the genetically engineered microorganism from which nanobodies are obtained are lyophilized.

In one embodiment, the nanobodies produced are immunotherapy agents. In another embodiment, the immunotherapy agent may be administered via injection (e.g., intravenously, intratumorally, subcutaneously, or into lymph nodes), but may also be administered orally, topically, or via aerosol. In an embodiment, the nanobody is employed to neutralize a virus. In one embodiment, the nanobodies are employed for a swabbing method to simultaneously sample and detect viruses on surfaces.

In one embodiment, the nanobody is an antiviral agent. In another embodiment, the immunotherapy agent is a vaccine. In one embodiment, the target antigen is a eukaryotic cell surface protein. In some embodiments, the eukaryotic cell surface protein is an immune checkpoint ligand.

In another embodiment, the disclosure provides a genetically engineered Wood-Ljungdahl bacterium comprising a disruptive mutation in one or more genes, wherein the genetically engineered bacterium has improved carbon flux through chorismate compared to a parental bacterium.

The one or more genes encode, for example, one or more of purine-nucleoside phosphorylase, lactate permease, cystathionine gamma-lyase, adenine phosphoribosyltransferase, 5'-nucleotidase/3'-nucleotidase/exopolyphosphatase, small conductance mechanosensitive channel, arginine deiminase, LL-diaminopimelate aminotransferase apoenzyme, and phosphopentomutase. In an embodiment, the expression of the one or more genes is decreased or eliminated compared to the parental bacterium.

In such an embodiment, the genetically engineered bacterium may produce a product such as chorismate, parahydroxybenzoic acid, salicylate, 2-aminobenzoate, dihydroxybenzoate, 4-hydroxycyclohexane carboxylic acid, and salts and ions thereof.

The disclosure also provides methods of producing products by culturing the microorganism of the disclosure in the presence of a substrate, such as a gaseous substrate comprising one or more of CO, $CO_2$, and/or $H_2$.

The term "non-naturally occurring" when used in reference to a microorganism is intended to mean that the microorganism has at least one genetic modification not found in a naturally occurring strain of the referenced species, including wild-type strains of the referenced species. Non-naturally occurring microorganisms are typically developed in a laboratory or research facility.

The terms "genetic modification," "genetic alteration," or "genetic engineering" broadly refer to manipulation of the genome or nucleic acids of a microorganism by the hand of man. Likewise, the terms "genetically modified," "genetically altered," or "genetically engineered" refers to a microorganism containing such a genetic modification, genetic alteration, or genetic engineering. These terms may be used to differentiate a lab-generated microorganism from a naturally-occurring microorganism. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

"Recombinant" indicates that a nucleic acid, protein, or microorganism is the product of genetic modification, engineering, or recombination. Generally, the term "recombinant" refers to a nucleic acid, protein, or microorganism that contains or is encoded by genetic material derived from multiple sources, such as two or more different strains or species of microorganisms.

"Wild type" refers to the typical form of an organism, strain, gene, or characteristic as it occurs in nature, as distinguished from mutant or variant forms.

"Endogenous" refers to a nucleic acid or protein that is present or expressed in the wild-type or parental microorganism from which the microorganism of the disclosure is derived. For example, an endogenous gene is a gene that is natively present in the wild-type or parental microorganism from which the microorganism of the disclosure is derived. In one embodiment, the expression of an endogenous gene may be controlled by an exogenous regulatory element, such as an exogenous promoter.

"Exogenous" refers to a nucleic acid or protein that originates outside the microorganism of the disclosure. For example, an exogenous gene or enzyme may be artificially or recombinantly created and introduced to or expressed in the microorganism of the disclosure. An exogenous gene or enzyme may also be isolated from a heterologous microorganism and introduced to or expressed in the microorganism of the disclosure. Exogenous nucleic acids may be adapted to integrate into the genome of the microorganism of the disclosure or to remain in an extra-chromosomal state in the microorganism of the disclosure, for example, in a plasmid. "Heterologous" refers to a nucleic acid or protein that is derived from a different strain or species and introduced to or expressed in the microorganism of the disclosure.

The terms "polynucleotide," "nucleotide," "nucleotide sequence," "nucleic acid," and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides or nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene products."

The terms "polypeptide", "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein, the term "amino acid" includes natural and/or unnatural or synthetic amino acids, including glycine and both the D or L optical isomers, and amino acid analogs and peptidomimetics.

"Enzyme activity," or simply "activity," refers broadly to enzymatic activity, including, but not limited to, the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" enzyme activity includes decreasing the activity of an enzyme, decreasing the amount of an enzyme, or decreasing the availability of an enzyme to catalyze a reaction.

"Mutated" refers to a nucleic acid or protein that has been modified in the microorganism of the disclosure compared to the wild-type or parental microorganism from which the microorganism of the disclosure is derived. In one embodiment, the mutation may be a deletion, insertion, or substitution in a gene encoding an enzyme. In another embodiment, the mutation may be a deletion, insertion, or substitution of one or more amino acids in an enzyme.

"Disrupted gene" refers to a gene that has been modified in some way to reduce or eliminate expression of the gene, regulatory activity of the gene, or activity of an encoded protein or enzyme. The disruption may partially inactivate, fully inactivate, or delete the gene or enzyme. The disruption may be a knockout (KO) mutation that fully eliminates the expression or activity of a gene, protein, or enzyme. The disruption may also be a knock-down that reduces, but does not entirely eliminate, the expression or activity of a gene, protein, or enzyme. The disruption may be anything that reduces, prevents, or blocks the biosynthesis of a product produced by an enzyme. The disruption may include, for example, a mutation in a gene encoding a protein or enzyme, a mutation in a genetic regulatory element involved in the expression of a gene encoding an enzyme, the introduction of a nucleic acid which produces a protein that reduces or inhibits the activity of an enzyme, or the introduction of a nucleic acid (e.g., antisense RNA, RNAi, TALEN, siRNA, CRISPR, or CRISPRi) or protein which inhibits the expression of a protein or enzyme. The disruption may be introduced using any method known in the art. For the purposes of the present disclosure, disruptions are laboratory-generated, not naturally occurring.

"Codon optimization" refers to the mutation of a nucleic acid, such as a gene, for optimized or improved translation of the nucleic acid in a particular strain or species. Codon optimization may result in faster translation rates or higher translation accuracy. In a preferred embodiment, the genes of the disclosure are codon optimized for expression in *Clostridium*, particularly *Clostridium autoethanogenum*, *Clostridium ljungdahlii*, or *Clostridium ragsdalei*. In a further preferred embodiment, the genes of the disclosure are codon optimized for expression in *Clostridium autoethanogenum* LZ1561, which is deposited under DSMZ accession number DSM23693.

"Overexpressed" refers to an increase in expression of a nucleic acid or protein in the microorganism of the disclosure compared to the wild-type or parental microorganism from which the microorganism of the disclosure is derived. Overexpression may be achieved by any means known in the art, including modifying gene copy number, gene transcription rate, gene translation rate, or enzyme degradation rate.

The term "variants" includes nucleic acids and proteins whose sequence varies from the sequence of a reference nucleic acid and protein, such as a sequence of a reference nucleic acid and protein disclosed in the prior art or exemplified herein. The disclosure may be practiced using variant nucleic acids or proteins that perform substantially the same function as the reference nucleic acid or protein. For example, a variant protein may perform substantially the same function or catalyze substantially the same reaction as a reference protein. A variant gene may encode the same or substantially the same protein as a reference gene. A variant promoter may have substantially the same ability to promote the expression of one or more genes as a reference promoter.

Such nucleic acids or proteins may be referred to herein as "functionally equivalent variants." By way of example, functionally equivalent variants of a nucleic acid may include allelic variants, fragments of a gene, mutated genes, polymorphisms, and the like. Homologous genes from other microorganisms are also examples of functionally equivalent variants. These include homologous genes in species such as *Clostridium acetobutylicum*, *Clostridium beijerinckii*, or *Clostridium ljungdahlii*, the details of which are publicly available on websites such as Genbank or NCBI. Functionally equivalent variants also include nucleic acids whose sequence varies as a result of codon optimization for a particular microorganism. A functionally equivalent variant of a nucleic acid will preferably have at least approximately 70%, approximately 80%, approximately 85%, approximately 90%, approximately 95%, approximately 98%, or greater nucleic acid sequence identity (percent homology) with the referenced nucleic acid. A functionally equivalent variant of a protein will preferably have at least approximately 70%, approximately 80%, approximately 85%, approximately 90%, approximately 95%, approximately 98%, or greater amino acid identity (percent homology) with the referenced protein. The functional equivalence of a variant nucleic acid or protein may be evaluated using any method known in the art.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

Nucleic acids may be delivered to a microorganism of the disclosure using any method known in the art. For example, nucleic acids may be delivered as naked nucleic acids or may be formulated with one or more agents, such as liposomes. The nucleic acids may be DNA, RNA, cDNA, or combinations thereof, as is appropriate. Restriction inhibitors may be used in certain embodiments. Additional vectors may include plasmids, viruses, bacteriophages, cosmids, and artificial chromosomes. In a preferred embodiment, nucleic acids are delivered to the microorganism of the disclosure using a plasmid. By way of example, transformation (including transduction or transfection) may be achieved by electroporation, ultrasonication, polyethylene glycol-mediated transformation, chemical or natural competence, protoplast transformation, prophage induction, or conjugation. In certain embodiments having active restriction enzyme systems, it may be necessary to methylate a nucleic acid before introduction of the nucleic acid into a microorganism.

Furthermore, nucleic acids may be designed to comprise a regulatory element, such as a promoter, to increase or otherwise control expression of a particular nucleic acid. The promoter may be a constitutive promoter or an inducible promoter. Ideally, the promoter is a Wood-Ljungdahl pathway promoter, a ferredoxin promoter, a pyruvate: ferredoxin oxidoreductase promoter, an Rnf complex operon promoter, an ATP synthase operon promoter, or a phosphotransacetylase/acetate kinase operon promoter.

A "microorganism" is a microscopic organism, especially a bacterium, archaea, virus, or fungus. The microorganism of the disclosure is typically a bacterium. Herein, recitation of "microorganism" should be taken to encompass "bacterium."

A "parental microorganism" is a microorganism used to generate a microorganism of the disclosure. The parental microorganism may be a naturally-occurring microorganism (i.e., a wild-type microorganism) or a microorganism that has been previously modified (i.e., a mutant or recombinant microorganism). The microorganism of the disclosure may be modified to express or overexpress one or more enzymes that were not expressed or overexpressed in the parental microorganism. Similarly, the microorganism of the disclosure may be modified to contain one or more genes that were not contained by the parental microorganism. The microorganism of the disclosure may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In a preferred embodiment, the parental microorganism is *Clostridium autoethanogenum* LZ1561, which was deposited on Jun. 7, 2010 with Deutsche Sammlung von Mikroorganismen und Zellkulturen GmbH (DSMZ) located at Inhoffenstraße 7B, D-38124 Braunschweig, Germany on Jun. 7, 2010 under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the disclosure is derived from a parental microorganism. In one embodiment, the microorganism of the disclosure is derived from *Clostridium autoethanogenum*, *Clostridium ljungdahlii*, or *Clostridium ragsdalei*. In a preferred embodiment, the microorganism of the disclosure is derived from *Clostridium autoethanogenum* LZ1561, which is deposited under DSMZ accession number DSM23693.

The microorganism of the disclosure may be further classified based on functional characteristics. For example, the microorganism of the disclosure may be or may be derived from a C1-fixing microorganism, an anaerobe, an acetogen, an ethanologen, a carboxydotroph, and/or a methanotroph. Table 1 provides a representative list of microorganisms and identifies their functional characteristics.

ability to produce one or more products from a C1-carbon source. Typically, the microorganism of the disclosure is a C1-fixing bacterium. In a preferred embodiment, the microorganism of the disclosure is derived from a C1-fixing microorganism identified in Table 1.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5% oxygen). Typically, the microorganism of the disclosure is an anaerobe. In a pre-

TABLE 1

|  | Wood-Ljungdahl | C1-fixing | Anaerobe | Acetogen | Ethanologen | Autotroph | Carboxydotroph |
|---|---|---|---|---|---|---|---|
| *Acetobacterium woodii* | + | + | + | + | +/− [1] | − | − |
| *Alkalibaculum bacchii* | + | + | + | + | + | + | + |
| *Blautia producta* | + | + | + | + | − | + | + |
| *Butyribacterium methylotrophicum* | + | + | + | + | + | + | + |
| *Clostridium aceticum* | + | + | + | + | − | + | + |
| *Clostridium autoethanogenum* | + | + | + | + | + | + | + |
| *Clostridium carboxidivorans* | + | + | + | + | + | + | + |
| *Clostridium coskatii* | + | + | + | + | + | + | + |
| *Clostridium drakei* | + | + | + | + | − | + | + |
| *Clostridium formicoaceticum* | + | + | + | + | − | + | + |
| *Clostridium ljungdahlii* | + | + | + | + | + | + | + |
| *Clostridium magnum* | + | + | + | + | − | + | +/− [2] |
| *Clostridium ragsdalei* | + | + | + | + | + | + | + |
| *Clostridium scatologenes* | + | + | + | + | − | + | + |
| *Eubacterium limosum* | + | + | + | + | − | + | + |
| *Moorella thermautotrophica* | + | + | + | + | + | + | + |
| *Moorella thermoacetica* (formerly *Clostridium thermoaceticum*) | + | + | + | + | − [3] | + | + |
| *Oxobacter pfennigii* | + | + | + | + | − | + | + |
| *Sporomusa ovata* | + | + | + | + | − | + | +/− [4] |
| *Sporomusa silvacetica* | + | + | + | + | − | + | +/− [5] |
| *Sporomusa sphaeroides* | + | + | + | + | − | + | +/− [6] |
| *Thermoanaerobacter kivui* | + | + | + | + | − | + | − |

[1] *Acetobacterium woodii* can produce ethanol from fructose, but not from gas.
[2] It has not been investigated whether *Clostridium magnum* can grow on CO.
[3] One strain of *Moorella thermoacetica*, *Moorella* sp. HUC22-1, has been reported to produce ethanol from gas.
[4] It has not been investigated whether *Sporomusa ovata* can grow on CO.
[5] It has not been investigated whether *Sporomusa silvacetica* can grow on CO.
[6] It has not been investigated whether *Sporomusa sphaeroides* can grow on CO.

"Wood-Ljungdahl" refers to the Wood-Ljungdahl pathway of carbon fixation as described. e.g., by Ragsdale, *Biochim Biophys Acta.* 1784: 1873-1898, 2008. "Wood-Ljungdahl microorganism" refers, predictably, to a microorganism containing the Wood-Ljungdahl pathway. The microorganism of the disclosure is a Wood-Ljungdahl microorganism, usually a Wood-Ljungdahl bacterium. Generally, the microorganism of the disclosure contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the disclosure. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ferred embodiment, the microorganism of the disclosure is derived from an anaerobe identified in Table 1.

An "acetogen" is a microorganism that produces or is capable of producing acetate (or acetic acid) as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta,* 1784: 1873-1898, 2008). Acetogens use the acetyl-CoA pathway as a (1) mechanism for the reductive synthesis of acetyl-CoA from $CO_2$. (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, NY, 2006). All naturally occurring acetogens are C1-fixing, anaerobic, autotrophic, and non-methanotrophic. Typically, the microorganism of the disclosure is an acetogen. In a preferred embodiment, the microorganism of the disclosure is derived from an acetogen identified in Table 1.

An "ethanologen" is a microorganism that produces or is capable of producing ethanol. Typically, the microorganism of the disclosure is an ethanologen. In a preferred embodiment, the microorganism of the disclosure is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the disclosure is an autotroph. In a preferred embodiment, the microorganism of the disclosure is derived from an autotroph identified in Table 1.

A "carboxydotroph" is a microorganism capable of utilizing CO as a sole source of carbon and energy. Typically, the microorganism of the disclosure is a carboxydotroph. In a preferred embodiment, the microorganism of the disclosure is derived from a carboxydotroph identified in Table 1.

A "methanotroph" is a microorganism capable of utilizing methane as a sole source of carbon and energy. In certain embodiments, the microorganism of the disclosure is a methanotroph or is derived from a methanotroph. In other embodiments, the microorganism of the disclosure is not a methanotroph or is not derived from a methanotroph.

More broadly, the microorganism of the disclosure may be derived from any genus or species identified in Table 1. For example, the microorganism may be a member of a genus selected from the group consisting of *Acetobacterium, Alkalibaculum, Blautia, Butyribacterium, Clostridium, Eubacterium, Moorella, Oxobacter, Sporomusa,* and *Thermoanaerobacter*. In particular, the microorganism may be derived from a parental bacterium selected from the group consisting of *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides,* and *Thermoanaerobacter kivui*.

In one embodiment, the microorganism of the disclosure is derived from the cluster of Clostridia comprising the species *Clostridium autoethanogenum, Clostridium ljungdahlii,* and *Clostridium ragsdalei*. These species were first reported and characterized by Abrini, Arch Microbiol, 161: 345-351, 1994 (*Clostridium autoethanogenum*), Tanner, *Int J System Bacteriol*, 43:232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 µm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng*. 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol*, 22:320-325, 2011).

Thus, in summary, many of the characteristics of *Clostridium autoethanogenum, Clostridium ljungdahlii,* or *Clostridium ragsdalei* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the disclosure may also be derived from an isolate or mutant of *Clostridium autoethanogenum, Clostridium ljungdahlii,* or *Clostridium ragsdalei*. Isolates and mutants of *Clostridium autoethanogenum* include JA1-1 (DSM10061) (Abrini, Arch Microbiol, 161:345-351, 1994), LBS1560 (DSM19630) (WO 2009/064200), and LZ1561 (DSM23693) (WO 2012/015317). Isolates and mutants of *Clostridium ljungdahlii* include ATCC 49587 (Tanner, Int J Syst Bacteriol, 43:232-236, 1993), PETCT (DSM13528, ATCC 55383), ERI-2 (ATCC 55380) (U.S. Pat. No. 5,593, 886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PHD thesis, North Carolina State University, 2010). Isolates and mutants of *Clostridium ragsdalei* include PI 1 (ATCC BAA-622, ATCC PTA-7826) (WO 2008/028055).

"Substrate" refers to a carbon and/or energy source for the microorganism of the disclosure. Typically, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the disclosure typically converts at least a portion of the CO in the substrate to a product. In some embodiments, the substrate comprises no or substantially no (<1 mol %) CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no (<1 mol %) $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no (<1 mol %) $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a byproduct of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The substrate and/or C1-carbon source may be a waste gas obtained as a byproduct of an industrial process or from another source, such as automobile exhaust fumes, biogas, landfill gas, direct air capture, or from electrolysis. The substrate and/or C1-carbon source may be syngas generated by pyrolysis, torrefaction, or gasification. In other words, carbon in waste material may be recycled by pyrolysis, torrefaction, or gasification to generate syngas which is used as the substrate and/or C1-carbon source. The substrate and/or C1-carbon source may be a gas comprising methane.

In certain embodiments, the industrial process is selected from ferrous metal products manufacturing, such as a steel manufacturing, non-ferrous products manufacturing, petroleum refining, electric power production, carbon black production, paper and pulp manufacturing, ammonia production, methanol production, coke manufacturing, petrochemical production, carbohydrate fermentation, cement making, aerobic digestion, anerobic digestion, catalytic processes, natural gas extraction, cellulosic fermentation, oil extraction, geological reservoirs, gas from fossil resources such as natural gas coal and oil, or any combination thereof. Examples of specific processing steps within an industrial process include catalyst regeneration, fluid catalyst cracking, and catalyst regeneration. Air separation and direct air capture are other suitable industrial processes. Specific examples in steel and ferroalloy manufacturing include blast furnace gas, basic oxygen furnace gas, coke oven gas, direct reduction of iron furnace top-gas, and residual gas from smelting iron. In these embodiments, the substrate and/or C1-carbon source may be captured from the industrial process before it is emitted into the atmosphere, using any known method.

The substrate and/or C1-carbon source may be synthesis gas known as syngas, which may be obtained from reforming, partial oxidation, or gasification processes. Examples of gasification processes include gasification of coal, gasification of refinery residues, gasification of petroleum coke, gasification of biomass, gasification of lignocellulosic material, gasification of waste wood, gasification of black liquor, gasification of municipal solid waste, gasification of municipal liquid waste, gasification of industrial solid waste, gasification of industrial liquid waste, gasification of refuse derived fuel, gasification of sewerage, gasification of sewerage sludge, gasification of sludge from wastewater treatment, gasification of biogas. Examples of reforming processes include, steam methane reforming, steam naphtha reforming, reforming of natural gas, reforming of biogas, reforming of landfill gas, naphtha reforming, and dry methane reforming. Examples of partial oxidation processes include thermal and catalytic partial oxidation processes, catalytic partial oxidation of natural gas, partial oxidation of hydrocarbons. Examples of municipal solid waste include tires, plastics, fibers, such as in shoes, apparel, and textiles. Municipal solid waste may be simply landfill-type waste. The municipal solid waste may be sorted or unsorted. Examples of biomass may include lignocellulosic material and may also include microbial biomass. Lignocellulosic material may include agriculture waste and forest waste.

The substrate and/or C1-carbon source may be a gas stream comprising methane. Such a methane containing gas may be obtained from fossil methane emission such as during fracking, wastewater treatment, livestock, agriculture, and municipal solid waste landfills. It is also envisioned that the methane may be burned to produce electricity or heat, and the C1 byproducts may be used as the substrate or carbon source.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

In certain embodiments, the fermentation is performed in the absence of carbohydrate substrates, such as sugar, starch, lignin, cellulose, or hemicellulose.

The microorganism of the disclosure may be cultured with the gaseous substrate to produce one or more products. For instance, the microorganism of the disclosure may produce or may be engineered to produce ethanol (WO 2007/117157), acetate (WO 2007/117157), 1-butanol (WO 2008/115080, WO 2012/053905, and WO 2017/066498), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2017/066498), 1-hexanol (WO 2017/066498), 1-octanol (WO 2017/066498), chorismate-derived products (WO 2016/191625), 3-hydroxybutyrate (WO 2017/066498), 1,3-butanediol (WO 2017/066498), 2-hydroxyisobutyrate or 2-hydroxyisobutyric acid (WO 2017/066498), isobutylene (WO 2017/066498), adipic acid (WO 2017/066498), 1,3-hexanediol (WO 2017/066498), 3-methyl-2-butanol (WO 2017/066498), 2-buten-1-ol (WO 2017/066498), isovalerate (WO 2017/066498), isoamyl alcohol (WO 2017/066498), and/or monoethylene glycol (WO 2019/126400) in addition to 2-phenylethanol. In certain embodiments, microbial biomass itself may be considered a product. These products may be further converted to produce at least one component of diesel, jet fuel, and/or gasoline. In certain embodiments, 2-phenylethanol may be used as an ingredient in fragrances, essential oils, flavors, and soaps. Additionally, the microbial biomass may be further processed to produce a single cell protein (c) by any method or combination of methods known in the art. In addition to one or more target products, the microorganism of the disclosure may also produce ethanol, acetate, and/or 2,3-butanediol.

At least one of the one or more fermentation products may be biomass produced by the culture. At least a portion of the microbial biomass may be converted to a single cell protein (SCP). At least a portion of the single cell protein may be utilized as a component of animal feed.

In one embodiment, the disclosure provides an animal feed comprising microbial biomass and at least one excipient, wherein the microbial biomass comprises a microorganism grown on a gaseous substrate comprising one or more of CO, $CO_2$, and $H_2$.

A "single cell protein" (SCP) refers to a microbial biomass that may be used in protein-rich human and/or animal feeds, often replacing conventional sources of protein supplementation such as soymeal or fishmeal. To produce a single cell protein, or other product, the process may comprise additional separation, processing, or treatments steps. For example, the method may comprise sterilizing the microbial biomass, centrifuging the microbial biomass, and/or drying the microbial biomass. In certain embodiments, the microbial biomass is dried using spray drying or paddle drying. The method may also comprise reducing the nucleic acid content of the microbial biomass using any method known in the art, since intake of a diet high in nucleic acid content may result in the accumulation of nucleic acid degradation products and/or gastrointestinal distress. The single cell protein may be suitable for feeding to animals, such as livestock or pets. In particular, the animal feed may be suitable for feeding to one or more beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents. The composition of the animal feed may be tailored to the nutritional requirements of different animals. Furthermore, the process may comprise blending or combining the microbial biomass with one or more excipients.

"Microbial biomass" refers biological material comprising microorganism cells. For example, microbial biomass may comprise or consist of a pure or substantially pure culture of a bacterium, archaea, virus, or fungus. When initially separated from a fermentation broth, microbial biomass generally contains a large amount of water. This water may be removed or reduced by drying or processing the microbial biomass.

An "excipient" may refer to any substance that may be added to the microbial biomass to enhance or alter the form, properties, or nutritional content of the animal feed. For example, the excipient may comprise one or more of a carbohydrate, fiber, fat, protein, vitamin, mineral, water, flavour, sweetener, antioxidant, enzyme, preservative, probiotic, or antibiotic. In some embodiments, the excipient may be hay, straw, silage, grains, oils or fats, or other plant material. The excipient may be any feed ingredient identified in Chiba, Section 18: Diet Formulation and Common Feed Ingredients, Animal Nutrition Handbook, $3^{rd}$ revision, pages 575-633, 2014.

A "biopolymer" refers to natural polymers produced by the cells of living organisms. In certain embodiments, the biopolymer is PHA. In certain embodiments, the biopolymer is PHB.

A "bioplastic" refers to plastic materials produced from renewable biomass sources. A bioplastic may be produced from renewable sources, such as vegetable fats and oils, corn starch, straw, woodchips, sawdust, or recycled food waste.

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism, but is not produced by a genetically unmodified microorganism from which the genetically modified microorganism is derived.

Herein, reference to an acid (e.g., acetic acid or 2-hydroxyisobutyric acid) should be taken to also include the corresponding salt (e.g., acetate or 2-hydroxyisobutyrate).

The product or co-product may comprise a nanobody.

"Selectivity" refers to the ratio of the production of a target product to the production of all fermentation products produced by a microorganism. The microorganism of the disclosure may be engineered to produce products at a certain selectivity or at a minimum selectivity. In one embodiment, a target product account for at least about 5%, 10%, 15%, 20%, 30%, 50%, or 75% of all fermentation products produced by the microorganism of the disclosure. In one embodiment, the target product accounts for at least 10% of all fermentation products produced by the microorganism of the disclosure, such that the microorganism of the disclosure has a selectivity for the target product of at least 10%. In another embodiment, the target product accounts for at least 30% of all fermentation products produced by the microorganism of the disclosure, such that the microorganism of the disclosure has a selectivity for the target product of at least 30%.

"Increasing the efficiency," "increased efficiency," and the like include, but are not limited to, increasing growth rate, product production rate or volume, product volume per volume of substrate consumed, or product selectivity. Efficiency may be measured relative to the performance of parental microorganism from which the microorganism of the disclosure is derived.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently the capital cost of the fermentation equipment.

In certain embodiments, the fermentation is performed in the absence of light or in the presence of an amount of light insufficient to meet the energetic requirements of photosynthetic microorganisms. In certain embodiments, the microorganism of the disclosure is a non-photosynthetic microorganism.

Target products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor. Purification techniques may include affinity tag purification (e.g. His, Twin-Strep, and FLAG), bead-based systems, a tip-based approach, and FPLC system for larger scale, automated purifications. Purification methods that do not rely on affinity tags (e.g. salting out, ion exchange, and size exclusion) are also disclosed.

The microorganism of the disclosure contains at least one disrupted gene. In some embodiments, the microorganism of the disclosure contains more than one disrupted genes, e.g., 2, 3, 4, 5, 6, 7, 8, 9, 10, 11, 12, 13, 14, 15, 16, 17, 18, 19, 20, 25, 30, 35, 40, 45, 50, 75, 100, or 200 disrupted genes. For example, the disrupted gene may be selected from Table 2. Although representative accession numbers are provided for *C. autoethanogenum*, *C. ljungdahlii*, and *C. ragsdalei*, a person of ordinary skill in the art would be capable of readily identifying homologs in other Wood-Ljungdahl microorganisms.

The inventors have further identified key metabolic pathways and key metabolic nodes in Wood-Ljungdahl microorganisms (FIG. 1). The disclosure further provides microorgansims with disrupted genes to strategically divert carbon flux is away from nonessential or undesirable metabolic nodes and through target metabolic nodes. Such strains have improved production of products downstream of those target metabolic nodes.

The disclosure finally provides methods of producing products by culturing the microorganism of the disclosure in the presence of a substrate, such as a gaseous substrate comprising one or more of CO, $CO_2$, and/or $H_2$. Possible combinations of disrupted genes for optimizing production of particular products are described in Examples.

As described elsewhere in this application, such products may include native or non-native products of Wood-Ljungdahl microorganisms. For example, such products include, but are not limited to acetyl-CoA, ethanol, acetate, butanol, butyrate, butyryl-CoA, 2,3-butanediol, lactate, butene, butadiene, methyl ethyl ketone, ethylene, acetone, isopropanol, lipids, 3-hydroxypropionate (3-HP), isoprene, farnesene, fatty acids (fatty acid ethyl esters, fatty acid butyl esters), 2-butanol, 1,2-propanediol, 1-propanol, chorismate-derived products, 3-hydroxybutyrate, 1,3-butanediol, C6-C8 alcohols (hexanol, heptanol, octanol), caproate, octanoate, isopentenyl pyrophosphate (IPP), dimethylallyl pyrophosphate (DMAPP), acetoacetyl-CoA, 3-hydroxybutyrate-CoA (3-HB-CoA), malonyl-CoA, pyruvate, dehydroshikimate, chorismate, para-hydroxybenzoic acid, salicylate, 2-aminobenzoate, 2,3-dihydroxybenzoate, 2-hydroxycyclohexane carboxylic acid, citramalate, ketobutyrate, acetolactate, acetoin, valine, leucine, and isoleucine.

EXAMPLES

The following examples further illustrate the methods and compositions of the disclosure but should not be construed to limit its scope in any way.

Example 1

This example describes metabolic modeling in Wood-Ljungdahl microorganisms.

A genome-scale metabolic model of *Clostridium autoethanogenum* like the one described by Marcellin, *Green Chem*, 18:3020-3028, 2016 was utilized. This model was used to simulate the design, construction, in silico growth and screening of strains with disruptive gene mutations to predict those that would produce higher yields of native compounds. In addition, new genome-scale models were built for a number non-native compound-producing strains. For these, heterologous genes and metabolic reactions were added to the wild type *Clostridium autoethanogenum* model structure to represent the incorporation of the non-native compound production pathway. Although the model used for the experimental work described herein is based on *Clostridium autoethanogenum*, the results can reasonably be expected to apply to other Wood-Ljungdahl microorganisms as well, given similarities in metabolism.

For each chemical production strain, millions of mutant strains incorporating different combinations of disruptive gene mutations were built in silico. Boolean gene-protein-reaction associations were used to determine which metabolic reactions were inactivated upon disruption of a gene (Thiele, Nature Protocols, 5:93-121, 2010). The design, construction and screening of mutant strains was carried out using cameo version 0.11.2 (Sonnenschein, Biosustain/Cameo: 0.11.0, doi: 10.5281/zenodo.835730, 2017) and evolutionary algorithms implemented by inspired version 1.0.1.

The growth of these mutant strains was simulated using two constraint-based computational modeling techniques: flux balance analysis (FBA) and linear minimization of metabolic adjustment (LMOMA). These growth simulation techniques are used to capture two likely metabolic phenotypes, following genetic perturbation (Maia, *Proceedings of the Genetic and Evolutionary Computation Conference Companion on—GECCO '17*, New York, New York, ACM Press, 1661-1668, 2017). An experimental metabolic flux profile was constructed and used as the reference state for LMOMA simulations. Growth simulations were run using scripts from cobrapy version 0.8.2 (Ebrahim., COBRApy: COnstraints-Based Reconstruction and Analysis for Python, *BMC Syst Biol*, 7:74, 2013), with optlang version 1.2.3 (Jensen, Optlang: An Algebraic Modeling Language for Mathematical Optimization," The Journal of Open Source Software, 2, doi: 10.21105/joss.00139, 2017) as the solver interface and Gurobi Optimizer version 7.0.2 as the optimization solver.

Growth rates and key metabolic fluxes including those for fermentation products were recorded and used to screen strains. For each strain simulation, the biomass-product coupled yield (BPCY) and the and the carbon molar yield were calculated. These yields were used to determine the fitness score.

In addition, flux variability analysis (FVA) was carried out to determine whether the mutant strain requires production of the compound of interest for growth to occur (growth-coupled strain designs). If the minimum boundary flux of the compound of interest was greater than zero during growth, the strain was classified as growth-coupling. These growth-coupled strain designs should allow greater fermentation stability during continuous fermentation. This minimum flux was converted to carbon yield (FVA minimum yield) and used to compare the level of growth coupling between strains.

Example 2

This example describes a genome-scale model (GEM) that allows the ability to predict the phenotype of an organism from its genotype and environmental conditions. This includes predicting feasible selectivity values for a molecule of interest. By applying constraint-based optimization algorithms to these models, identification of environmental and genetic changes that can be made to achieve a desired phenotype. For example, the model can identify gas-uptake rates required to achieve high selectivity to a chemical of interest. For more information on genome-scale modelling, see O'Brien et al. (2015). Additionally, a metabolism and expression model (ME-model) which incorporates transcription, translation and enzyme-complex formation reactions is constructed. An ME-model of another acetogenic microorganism, *C. ljungdahlii*, has also recently been published (Liu et al., 2019).

GEM augmented with an ME-model pathway representation of nanobody formation. This approach may be used because the *Clostridium autoethanogenum* GEM already accounts for the growth- and non-growth-associated demands of the native *Clostridium autoethanogenum* cell while the additional ME-model pathway will represent the additional metabolic cost of nanobody production. Briefly, the ME-model pathway will consist of reaction stoichiometries representing: 1) the transcription of the nanobody-encoding gene(s) to mRNA based on the nucleotide composition of the corresponding nanobody-encoding gene sequence(s); 2) the translation of the nanobody-encoding mRNA based on the corresponding mRNA composition and tRNA availability; and 3) the formation of the nanobody complex, based on the structure/subunit-composition and cofactor requirements of the target nanobody. The 'reactions' comprising these ME-model pathways form part of the metabolic model and on analysis will be associated with a reaction-rate, or 'flux.' This means that values representing metabolic flux towards nanobody production can be calculated.

Constraint-based optimization to analyze the model of nanobody production is implemented. This requires setting a series of constraints that represent the growth conditions of *Clostridium autoethanogenum* (primarily nutrient availability and growth rate) while optimizing for an objective of interest. Maximizing feasible rates of nanobody production while constraining a range of gas uptake and co-production rates will be implemented. The results of this analysis include optimal rates of production of nanobody which satisfy the constrains. This approach establishes plausible performance of a nanobody-producing strain of *Clostridium autoethanogenum*.

Example 3

This example describes gene disruption targets common across different product pathways. Optimizations were run using an evolutionary algorithm on 444 pathways. Each strain design was scored based on the achieved yield (non-growth coupled designs) and biomass-product coupled yield (growth coupled designs). Each gene was ranked based on how often it appeared in strain designs. 19 genes were commonly identified for disruption in optimized strains.

| # | Gene | Growth coupling score | Non-growth coupling score | Total score |
|---|---|---|---|---|
| 1 | CAETHG_3359 | 6.039281 | 14.18996 | 20.22924 |
| 2 | CAETHG_2932 | 0 | 16.79651 | 16.79651 |
| 3 | CAETHG_3293 | 2.508019 | 13.12476 | 15.63278 |
| 4 | CAETHG_3510 | 0 | 12.77112 | 12.77112 |
| 5 | CAETHG_3924 | 0 | 11.15045 | 11.15045 |
| 6 | CAETHG_1371 | 0 | 11.03476 | 11.03476 |
| 7 | CAETHG_2006 | 0 | 10.68385 | 10.68385 |
| 8 | CAETHG_2909 | 1.515088 | 8.61957 | 10.13466 |
| 9 | CAETHG_2721 | 0 | 9.82919 | 9.82919 |
| 10 | CAETHG_2753 | 0.50272 | 9.082944 | 9.585664 |
| 11 | CAETHG_0160 | 0 | 8.767024 | 8.767024 |
| 12 | CAETHG_3299 | 0 | 7.876761 | 7.876761 |
| 13 | CAETHG_2751 | 4.149778 | 3.457399 | 7.607177 |
| 14 | CAETHG_0233 | 0 | 7.516631 | 7.516631 |
| 15 | CAETHG_1270 | 0 | 7.501854 | 7.501854 |

-continued

| # | Gene | Growth coupling score | Non-growth coupling score | Total score |
|---|------|---|---|---|
| 16 | CAETHG_0234 | 0 | 7.213378 | 7.213378 |
| 17 | CAETHG_2790 | 0 | 6.668087 | 6.668087 |
| 18 | CAETHG_2791 | 0 | 6.554927 | 6.554927 |
| 19 | CAETHG_2796 | 0 | 6.324132 | 6.324132 |

Example 4

This example describes gene disruption targets to increase target compound production during autotrophic growth. This strategy involves eliminating or decreasing the production of other fermentation byproducts, making the target compound a required growth byproduct. Metabolic modeling experiments were performed as described in Example 1.

Modeling evidence demonstrates that this strategy is appropriate for target compounds whose production imposes minimal ATP burden. This strategy is not well suited for products with significant ATP burden during autotrophic growth. This is because this strategy decreases cellular ATP yields through the elimination of substrate level phosphorylation catalysed by acetate kinase.

In particular, production of products such as acetone, isopropanol, 1,3-butanediol, 3-hydroxybutyrate, 2-hydroxyisobutyrate, 3-hydroxyisovalerate, and adipic acid can be improved by introducing a disruptive mutation into genes encoding acetate kinase and/or phosphate transacetylase, and optionally further introducing a disruptive mutation into one or more genes encoding acetolactate decarboxylase, lactate dehydrogenase, aldehyde dehydrogenase, or citramalate synthase.

Each model was assessed using flux variability analysis to determine the minimum required flux towards the target compound during normal growth. Then, the proposed set of disruptive gene mutations was applied to each model. Flux variability analysis was carried out again to identify any existence of coupling between compound production and growth. Simulations were carried out using cobrapy version 0.13.4.

| Product | Minimum yield during cell growth | Minimum yield during cell growth with target genes disrupted |
|---|---|---|
| Acetone | 0.00 | 0.301 |
| 1,3-Butanediol | 0.00 | 0.323 |
| 3-Hydroxybutyrate | 0.00 | 0.395 |
| 2-Hydroxyisobutyrate | 0.00 | 0.395 |
| 3-Hydroxyisovalerate | 0.00 | 0.368 |
| Adipic acid | 0.00 | 0.428 |

Example 5

This example describes increasing target compound production during autotrophic growth on gas mixes with a low proportion of CO by decreasing required acetate co-production. Metabolic modeling experiments were performed as described in Example 1.

The strategy involves adjusting the redox cofactor balance so there is excess NADPH. To maintain redox homeostasis, the cell must make products whose production pathway requires NADPH. As acetate production does not fulfil this, the cell will be required to make other products to achieve maximum growth rates.

Modeling evidence demonstrates that this strategy is appropriate for target compounds with an ATP burden that requires the co-production of acetate. This strategy is also appropriate for strains that produce ethanol as a primary product. This strategy is predicted to work on low CO gases, where the cell can utilise the hydrogenase enzyme to reduce ferredoxin and NAD (P)+. In some cases, the maximum possible yield of the target compound will decrease, as this strategy reduces the efficiency of the energy metabolism of the cell.

In particular, production of products and/or co-products such as ethanol, acetone, isopropanol, 1,3-butanediol, 2-butanol, 2-hydroxyisobutyrate, 3-hydroxyisovalerate, adipic acid, methyl ethyl ketone, isoprene, salicylate, chorismate, and farnesene can be improved by introducing a disruptive mutation into a gene encoding NAD-dependent electron-bifurcating [FeFe]-hydrogenase (e.g., Hyd), and optionally further introducing a disruptive mutation into one or more genes encoding glutamate synthase, citramalate synthase, acetolactate decarboxylase, or lactate dehydrogenase.

Each model was assessed using flux variability analysis to determine the minimum required flux to acetate at high growth rates. Then, the proposed set of disruptive gene mutations was applied to each model. The NAD-dependent hydrogenase (Hyd) was removed from the stoichiometric matrix to represent the knock out of this enzyme. Flux through the glutamate synthase reaction was decreased by 30% to represent a disruption of this enzyme. Flux variability analysis was carried out again to determine the minimum acetate production requirement to achieve maximum growth. Simulations were carried out using cobrapy version 0.13.4

| | Minimum required acetate yield at highest growth rate (C-mol product/mol CO + $H_2$ uptake) | | |
|---|---|---|---|
| Product | Parental strain | Disrupted NAD-dependent electron-bifurcating [FeFe]-hydrogenase (Hyd) | Disrupted NAD-dependent electron-bifurcating [FeFe]-hydrogenase (Hyd) and disrupted glutamate synthase (under expression) |
| Ethanol | 0.430 | 0.356 | 0.0002 |
| Acetone | 0.430 | 0.356 | 0.0002 |
| Isopropanol | 0.430 | 0.356 | 0.0002 |
| 1,3-Butanediol | 0.430 | 0.356 | 0.0000 |
| 2-Butanol | 0.430 | 0.356 | 0.0002 |
| 2-Hydroxyisobutyrate | 0.430 | 0.356 | 0.0000 |
| 3-Hydroxyisovalerate | 0.430 | 0.356 | 0.0000 |
| Adipic acid | 0.430 | 0.356 | 0.0002 |
| Methyl ethyl ketone | 0.430 | 0.356 | 0.0002 |
| Isoprene | 0.430 | 0.355 | 0.0000 |
| Salicylate | 0.430 | 0.356 | 0.0002 |
| Chorismate | 0.430 | 0.356 | 0.0002 |
| Farnesene | 0.430 | 0.356 | 0.0002 |

Example 6

This example describes increasing flux through acetoacetyl-CoA, a central metabolic node. Increasing flux through this node will increase production of downstream products and/or co-products such as acetone, isopropanol, 3-hydroxyisovaleryl-CoA, 3-hydroxyisovalerate, isobutylene, isopentenyl pyrophosphate (IPP), dimethylallyl pyrophosphate (DMAPP), isoprene, terpenoids such as farnesene, 3-hydroxybutyryl-CoA, crotonyl-CoA, 3-hydroxybutyrate, 3-hydroxybutyrylaldehyde, 1,3-butanediol, 2-hydroxyisobutyryl-CoA, 2-hydroxyisobutyrate, butyryl-CoA, butyrate, butanol, caproate, hexanol, octanoate, octanol, 1,3-hexanediol, 2-buten-1-ol, isovaleryl-CoA, isovalerate, or isoamyl alcohol. Metabolic modeling experiments were performed as described in Example 1.

Most Wood-Ljungdahl microorganisms are not natively capable of converting acetyl-CoA to acetoacetyl-CoA, such that this step may require the introduction of a heterologous enzyme, such as a thiolase (i.e., acetyl-CoA acetyltransferase) (EC 2.3.1.9). The thiolase may be, for example, ThlA from *Clostridium acetobutylicum* (WP_010966157.1), PhaA from *Cupriavidus necator* (WP_013956452.1), BktB from *Cupriavidus necator* (WP_011615089.1), AtoB from *Escherichia coli* (NP_416728.1), or a similar.

In particular, flux through acetoacetyl-CoA can be improved by introducing a disruptive mutation into one or more genes encoding one or more, two or more, three or more, four or more, or five or more of NAD-dependent electron-bifurcating [FeFe]-hydrogenase (e.g., Hyd), glutamate synthase, citramalate synthase, acetolactate decarboxylase, lactate dehydrogenase, acetate kinase, phosphate transacetylase, or aldehyde dehydrogenase.

| Enzyme name | Reference number in *C. autoethanogenum* |
|---|---|
| NAD-dependent electron-bifurcating [FeFe]-hydrogenase | CAETHG_1576, CAETHG_1578, CAETHG_3569, CAETHG_3570, CAETHG_3571 |
| Glutamate synthase | CAETHG_0477, CAETHG_1580, CAETHG_3850, CAETHG_3851 |
| Citramalate synthase | CAETHG_2751 |
| Acetolactate decarboxylase | CAETHG_2932 |
| Lactate dehydrogenase | CAETHG_1147 |
| Acetate kinase | CAETHG_3359 |
| Phosphate transacetylase | CAETHG_3358 |
| Aldehyde dehydrogenase | CAETHG_1819, CAETHG_3287, CAETHG_1830 |

Example 7

Genes encoding nanobodies (Table 2) were synthesized and assembled into *Clostridium-E. coli* shuttle vector pMTL8225 (Heap, J Microbiol Methods 78:79-85, 2009). The genes contain DNA encoding a start codon as well as a C-terminal twin-strep tag as a handle for protein detection via Western Blot and/or affinity purification (Schmidt, Protein Expr Purif 92:54-61, 2013. These vectors have a pre-cloned clostridial promoter $P_{fer}$ and terminator. The promoter sequence is described in Karim et al. Synthetic Biology 2020; 5 (1): ysaa019. The resulting plasmids have an ermB antibiotic selectable marker.

After transformation into *Clostridium autoethanogenum*, growth experiments were conducted in 12-well plates with 2 mL minimal media and 200 kPa of synthetic gas mix (50% CO, 10% $H_2$, 30% $CO_2$, and 10% $N_2$) at 37° C. until biomass concentration reached 0.15-0.32 gDCW/L. The biomass was pelleted and frozen for further analysis. Sequencing confirmed the identity of the nanobody DNA in the strains.

Figure 2:
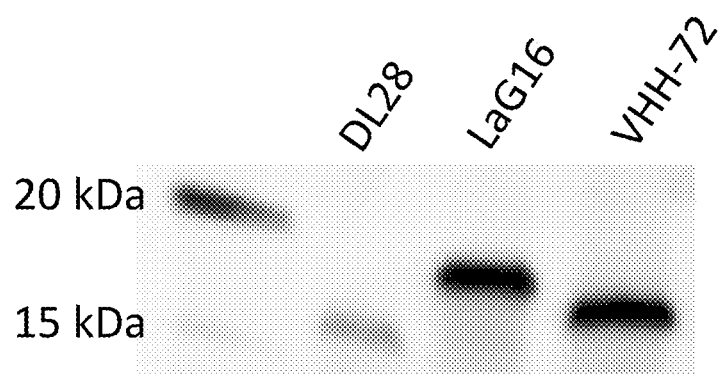
FIG. 2 demonstrates nanobodies with C-terminal twin-strep tag was evaluated for expression in *Clostridium autoethanogenum* by Western blot with anti-strep tag antibodies.

Nanobody presence and integrity was verified by Western blot using anti-strep tag detection (FIG. 2). Whole pellets were prepared by boiling in tricine sample buffer and run on a 16.5% tris-tricine SDS PAGE gel (Bio-Rad, Hercules, CA). The protein bands were electrophoretically transferred to nitrocellulose membrane (Bio-Rad, Hercules, CA) then blocked overnight in SuperBlock blocking buffer (Thermo Fisher Scientific, Waltham MA). The membrane was prepared and probed with anti-strep tag antibodies conjugated to horseradish peroxidase according to the manufacturer's instructions (Strep-Tactin HRP Conjugate, IBA Lifesciences, Göttingen, Germany). Chemiluminescence was used to reveal bands (Western Lightning Plus, PerkinElmer, Waltham, MA). Western blot showed single band nanobodies between 15 kDa and 20 kDa.

TABLE 2

| SEQ ID NO: | Description | Sequence |
|---|---|---|
| 1 | DL28 SARS Cov2 (includes start codon and twin-strep tag) | MAQVQLQESGGGLVQAGGSLRLSCAASGSDFSSSTMGWYRQAPGK QREFVAISSEGSTSYAGSVKGRFTISRDNAKNTVYLQMNSLEPEDTAVY YCNVVDRWYDYWGQGTQVTVSGGSGGGSGWSHPQFEKGGGSGG GSGGSSAWSHPQFEK |
| 2 | DL28 SARS Cov2 (Li preprint doi.org/10.1101/ 2021.07.20.453054) | QVQLQESGGGLVQAGGSLRLSCAASGSDFSSSTMGWYRQAPGKQRE FVAISSEGSTSYAGSVKGRFTISRDNAKNTVYLQMNSLEPEDTAVYYCN VVDRWYDYWGQGTQVTVS |
| 3 | LaG16 (includes start codon and twin-strep tag) | MAQVQLVESGGGRLVQAGDSLRLSCAASGRTFSTSAMAWFRQAPGRE REFVAAITWTVGNTILGDSVKGRFTISRDRAKNTVDLQMDNLEPEDTA VYYCSARSRGYVLSVLRSVDSYDYWGQGTQVTVSGGSGGGSGWSHP QFEKGGGSGGGSGGSSAWSHPQFEK |
| 4 | LaG16 (Fridy et al Nature Methods 2014 11(12):1253-1260) | MAQVQLVESGGGRLVQAGDSLRLSCAASGRTFSTSAMAWFRQAPGRE REFVAAITWTVGNTILGDSVKGRFTISRDRAKNTVDLQMDNLEPEDTA VYYCSARSRGYVLSVLRSVDSYDYWGQGTQVTVS |
| 5 | VHH-72 SARS Cov2 (includes start codon and twin-strep tag) | MAQVQLQESGGGLVQAGGSLRLSCAASGRTFSEYAMGWFRQAPGK EREFVATISWSGGSTYYTDSVKGRFTISRDNAKNTVYLQMNSLKPDDT AVYYCAAAGLGTVVSEWDYDYDYWGQGTQVTVSSGSGGSGGGSG WSHPQFEKGGGSGGGSGGSSAWSHPQFEK |

TABLE 2-continued

| SEQ ID NO: | Description | Sequence |
|---|---|---|
| 6 | VHH-72 SARS Cov2 (Wrapp et al 2020 Cell 181, 1004-1015) | QVQLQESGGGLVQAGGSLRLSCAASGRTFSEYAMGWFRQAPGKERE FVATISWSGGSTYYTDSVKGRFTISRDNAKNTVYLQMNSLKPDDTAVY YCAAAGLGTVVSEWDYDYWGQGTQVTVSS |

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means ±20% of the indicated range, value, or structure, unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

SEQUENCE LISTING

```
Sequence total quantity: 6
SEQ ID NO: 1            moltype = AA  length = 152
FEATURE                 Location/Qualifiers
source                  1..152
                        mol_type = protein
                        organism = Vicugna pacos
SEQUENCE: 1
MAQVQLQESG GGLVQAGGSL RLSCAASGSD FSSSTMGWYR QAPGKQREFV AISSEGSTSY    60
AGSVKGRFTI SRDNAKNTVY LQMNSLEPED TAVYYCNVVD RWYDYWGQGT QVTVSGGSGG   120
GSGWSHPQFE KGGGSGGGSG GSSAWSHPQF EK                                 152

SEQ ID NO: 2            moltype = AA  length = 113
FEATURE                 Location/Qualifiers
source                  1..113
                        mol_type = protein
                        organism = Vicugna pacos
SEQUENCE: 2
QVQLQESGGG LVQAGGSLRL SCAASGSDFS SSTMGWYRQA PGKQREFVAI SSEGSTSYAG    60
SVKGRFTISR DNAKNTVYLQ MNSLEPEDTA VYYCNVVDRW YDYWGQGTQV TVS          113

SEQ ID NO: 3            moltype = AA  length = 165
FEATURE                 Location/Qualifiers
source                  1..165
                        mol_type = protein
                        organism = Lama glama
SEQUENCE: 3
MAQVQLVESG GRLVQAGDSL RLSCAASGRT FSTSAMAWFR QAPGREREFV AAITWTVGNT    60
```

-continued

```
ILGDSVKGRF TISRDRAKNT VDLQMDNLEP EDTAVYYCSA RSRGYVLSVL RSVDSYDYWG    120
QGTQVTVSGG SGGGSGWSHP QFEKGGGSGG GSGGSSAWSH PQFEK                   165

SEQ ID NO: 4              moltype = AA  length = 128
FEATURE                   Location/Qualifiers
source                    1..128
                          mol_type = protein
                          organism = Lama glama
SEQUENCE: 4
MAQVQLVESG GRLVQAGDSL RLSCAASGRT FSTSAMAWFR QAPGREREFV AAITWTVGNT    60
ILGDSVKGRF TISRDRAKNT VDLQMDNLEP EDTAVYYCSA RSRGYVLSVL RSVDSYDYWG    120
QGTQVTVS                                                            128

SEQ ID NO: 5              moltype = AA  length = 166
FEATURE                   Location/Qualifiers
source                    1..166
                          mol_type = protein
                          organism = Lama glama
SEQUENCE: 5
MAQVQLQESG GGLVQAGGSL RLSCAASGRT FSEYAMGWFR QAPGKEREFV ATISWSGGST    60
YYTDSVKGRF TISRDNAKNT VYLQMNSLKP DDTAVYYCAA AGLGTVVSEW DYDYDYWGQG    120
TQVTVSSGSG SGGGSGWSH PQFEKGGGSG GGSGGSSAWS HPQFEK                   166

SEQ ID NO: 6              moltype = AA  length = 125
FEATURE                   Location/Qualifiers
source                    1..125
                          mol_type = protein
                          organism = Lama glama
SEQUENCE: 6
QVQLQESGGG LVQAGGSLRL SCAASGRTFS EYAMGWFRQA PGKEREFVAT ISWSGGSTYY    60
TDSVKGRFTI SRDNAKNTVY LQMNSLKPDD TAVYYCAAAG LGTVVSEWDY DYDYWGQGTQ    120
VTVSS                                                               125
```

The invention claimed is:

1. A genetically engineered C1-fixing microorganism capable of co-producing at least one target product and a nanobody comprising an exogenous nucleic acid encoding a nanobody gene, wherein the genetically engineered C1-fixing microorganism has improved carbon flux through acetoacetyl-CoA compared to a parental microorganism, wherein the nanobody gene is VHH-72 SARS Cov2.

2. The genetically engineered C1-fixing microorganism of claim 1, wherein the at least one target product is selected from the group 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, chorismate-derived products, 3-hydroxybutyrate, 1,3-butanediol, 2-hydroxyisobutyrate or 2-hydroxyisobutyric acid, isobutylene, adipic acid, keto-adipic acid, 1,3-hexanediol, 3-methyl-2-butanol, 2-buten-1-ol, isovalerate, isoamyl alcohol, and monoethylene glycol.

3. The genetically engineered C1-fixing microorganism of claim 1, wherein the nanobody is contained in the microorganism.

4. The genetically engineered C1-fixing microorganism of claim 1, further comprising a disruptive mutation in one or more genes.

5. The genetically engineered C1-fixing microorganism of claim 1, wherein the parental microorganism is selected from the group consisting of *Acetobacterium woodii*, *Alkalibaculum bacchii*, *Blautia producta*, *Butyribacterium methylotrophicum*, *Clostridium aceticum*, *Clostridium autoethanogemum*, *Clostridium carboxidivorans*, *Clostridium coskatii*, *Clostridium drakei*, *Clostridium formicoaceticum*, *Clostridium ljungdahlii*, *Clostridium magmnum*, *Clostridium ragsdalei*, *Clostridium scatologenes*, *Eubacterium limosum*, *Moorella thermautotrophica*, *Moorella thermoacetica*, *Oxobacter pfennigii*, *Sporomusa ovata*, *Sporomusa silvacetica*, *Sporomusa sphaeroides*, *Cupriavidus necator* and *Thermoanaerobacter kivui*.

6. The genetically engineered C1-fixing microorganism of claim 1, wherein the parental microorganism is selected from the group consisting of *Clostridium* autoethanogemum, *Clostridium ljungdahlii*, and *Clostridium ragsdalei*.

7. A method of co-producing at least one target product and a nanobody by culturing the genetically engineered C1-fixing microorganism of claim 1 in the presence of a gaseous substrate comprising one or more of CO, $CO_2$, and $H_2$.

8. The method of claim 7, wherein the at least one target product is selected from the group 1-butanol, butyrate, butene, butadiene, methyl ethyl ketone, ethylene, acetone, isopropanol, lipids, 3-hydroxypropionate, terpenes, isoprene, fatty acids, 2-butanol, 1,2-propanediol, 1-propanol, 1-hexanol, 1-octanol, chorismate-derived products, 3-hydroxybutyrate, 1,3-butanediol, 2-hydroxyisobutyrate or 2-hydroxyisobutyric acid, isobutylene, adipic acid, keto-adipic acid, 1,3-hexanediol, 3-methyl-2-butanol, 2-buten-1-ol, isovalerate, isoamyl alcohol, or monoethylene glycol.

* * * * *